(12) United States Patent
Churchill et al.

(10) Patent No.: US 8,901,158 B2
(45) Date of Patent: Dec. 2, 2014

(54) TREATMENT OF BIPOLAR DISORDER

(75) Inventors: Grant C. Churchill, Oxford (GB);
Sridhar R. Vasudevan, Oxford (GB);
Nisha Singh, Oxford (GB)

(73) Assignee: Isis Innovation Ltd., Oxford (GB)

( * ) Notice: Subject to any disclaimer, the term of this patent is extended or adjusted under 35 U.S.C. 154(b) by 0 days.

(21) Appl. No.: 13/983,011

(22) PCT Filed: Jan. 18, 2012

(86) PCT No.: PCT/GB2012/050105
§ 371 (c)(1),
(2), (4) Date: Dec. 13, 2013

(87) PCT Pub. No.: WO2012/107735
PCT Pub. Date: Aug. 16, 2012

(65) Prior Publication Data
US 2014/0094449 A1    Apr. 3, 2014

(30) Foreign Application Priority Data
Feb. 9, 2011 (GB) .................................. 1102248.0

(51) Int. Cl.
| | | |
|---|---|---|
| *A61K 31/428* | (2006.01) | |
| *A61K 31/416* | (2006.01) | |
| *A61K 31/41* | (2006.01) | |
| *A61K 45/06* | (2006.01) | |
| *C07D 275/04* | (2006.01) | |
| *C07D 293/12* | (2006.01) | |

(52) U.S. Cl.
CPC .............. *A61K 31/428* (2013.01); *A61K 31/416* (2013.01); *A61K 31/41* (2013.01); *A61K 45/06* (2013.01); *C07D 275/04* (2013.01); *C07D 293/12* (2013.01)
USPC ........................................................ 514/373

(58) Field of Classification Search
CPC ................................................... A61K 31/428
USPC ........................................................ 514/373
See application file for complete search history.

(56) References Cited

U.S. PATENT DOCUMENTS

| | | | |
|---|---|---|---|
| 4,981,980 A | 1/1991 | Giocobbe et al. | |
| 5,948,800 A | 9/1999 | Maruyama et al. | |

FOREIGN PATENT DOCUMENTS

| | | |
|---|---|---|
| JP | 2008007446 | 1/2008 |
| WO | 93/16073 A1 | 8/1993 |
| WO | 96/37197 A1 | 11/1996 |
| WO | 00/59489 A2 | 10/2000 |
| WO | 2004/037820 A1 | 5/2004 |
| WO | 2008/132139 A2 | 11/2008 |
| WO | 2009138987 A2 | 11/2009 |

OTHER PUBLICATIONS

King, Med. Chem. Principle and Practice (1994), pp. 206-208.*
International Search Report for priority application PCT/GB2012/050105 mailed Nov. 9, 2012.
Search Report for corresponding priority application No. GB1102248.0.
Posser T. et al.; "Antidepressant-like effect of the organoselenium compound ebselen in mice: Evidence for the involvement of the monoaminergic system", European Journal of Pharmacology, 602 (2009), pp. 85-91.
Berridge M. et al.; "Neural and Developmental Actions of Lithium: A Unifying Hypothesis", Cell, vol. 59, pp. 411-419, Nov. 3, 1989.
Singh et al.; "Inositol monophosphatase: drug target or false alarm?", 2010, XP002686121.
Atack J R; "Inositol monophosphatase inhibitors: Lithium mimetics?" Medicinal Research Reviews, New York, NY, vol. 17, No. 2, Jan. 1, 1997, pp. 215-224, XP002378586.
Atack J R et al.; "Inositol monophosphatase: A putative target for Li+ in the treatment of bipolar disorder"; Trends in Neurosciences, vol. 18, No. 8, 1995, pp. 343-349, XP002686122.
Harris R A et al.; "Sweet and Sour—oxidative and carbonyl stress in neurological disorders"; CNS and Neurological Disorders—Drug Targets 2011 Bentham Science Publishers, vol. 10, No. 1, Feb. 1, 2011, pp. 82-107, XP009161384.

(Continued)

*Primary Examiner* — Taofiq A Solola
(74) *Attorney, Agent, or Firm* — Wood, Phillips, Katz, Clark & Mortimer (57) ABSTRACT

The invention relates to sulphur- and/or selenium-containing compounds that can inhibit the enzyme inositol mono-phosphatase (IMPase), and which can be used in treating conditions that are treatable through inhibition of this enzyme, such as bi-polar disorder, the compounds having a structure of Formula (I), or is a pharmaceutically acceptable salt thereof; Formula (I); in which: E is S or Se and each of phenyl rings A and B is optionally substituted with one or more substituents, in which each substituent is selected independently from: (1) a halogen, which is preferably selected from F, Cl and Br; (2) $C_1$-$C_4$ alkyl, such as $C_1$-$C_2$ alkyl or $C_1$ alkyl, optionally substituted with one or more halogen atoms, each of which is preferably selected from F, Cl and Br; and (3) $C_1$-$C_4$ alkoxy, such as $C_1$-$C_2$ alkoxy or $C_1$ alkoxy; optionally substituted with one or more halogen atoms, each of which is preferably selected from F, Cl and Br.

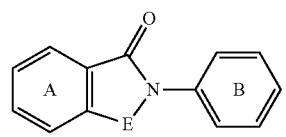

Formula I

14 Claims, 7 Drawing Sheets

(56) References Cited

OTHER PUBLICATIONS

Sarkar Sovan et al.; "Inositol and IP3 levels regulate autophagy: biology and therapeutic speculations"; Autophagy, Landes Bioscience, US, vol. 2, No. 2, Apr. 1, 2006, pp. 132-134, XP009151059.

Antoniadu et al.; "Effect of ebselen, a putative lithium-mimetic on central 5HT2A receptor function in the mouse"; Dec. 13, 2011, XP002686124.

Sanmartin C et al.; "Selenium and clinical trials: New therapeutic evidence for multiple diseases"; Current Medicinal Chemistry 2011, Betham Science Publishers, vol. 18, No. 30, Oct. 2011, pp. 4635-4650, XP002686125.

Sconzo G et al.; "Effect of the IMPase inhibitor L690,330 on sea urchin development"; Cell Biology International, vol. 22, No. 2, 1998, pp. 91-94, XP002686126.

* cited by examiner

TREATMENT OF BIPOLAR DISORDER

FIELD OF THE INVENTION

The present invention relates to the treatment of conditions that are treatable by inhibition of the enzyme inositol monophosphatase (IMPase), such as bipolar disorder, and to a compound and medicaments comprising the compound that can be used in the treatment of such conditions.

BACKGROUND OF THE INVENTION

Bipolar disorder is one of the most important causes of disability in people between the ages of 15 and 44. It is characterised by recurrent episodes of mania or elevated mood, and irritable or depressive moods. It is distinct from other mood disorders, for example depressive illnesses such as depression or recurrent depression, manic disorders such as mania or hypomania, or persistent mood disorders such as cyclothymia and dysthymia, being separately classified in the World Health Organisation's International Statistical Classification of Diseases and Related Health Problems.

Present treatments include valproic acid, lamotrigine, carbamazepine and lithium in the form of salts such as lithium carbonate or lithium citrate. Although generally considered to be the most effective treatment, lithium suffers from the problem of toxicity, its toxic level being only twice that of its therapeutic concentration. It can also cause side effects such as polyurea, polydypsia, and kidney damage, in addition to interfering with glucose metabolism.

Figure 1:
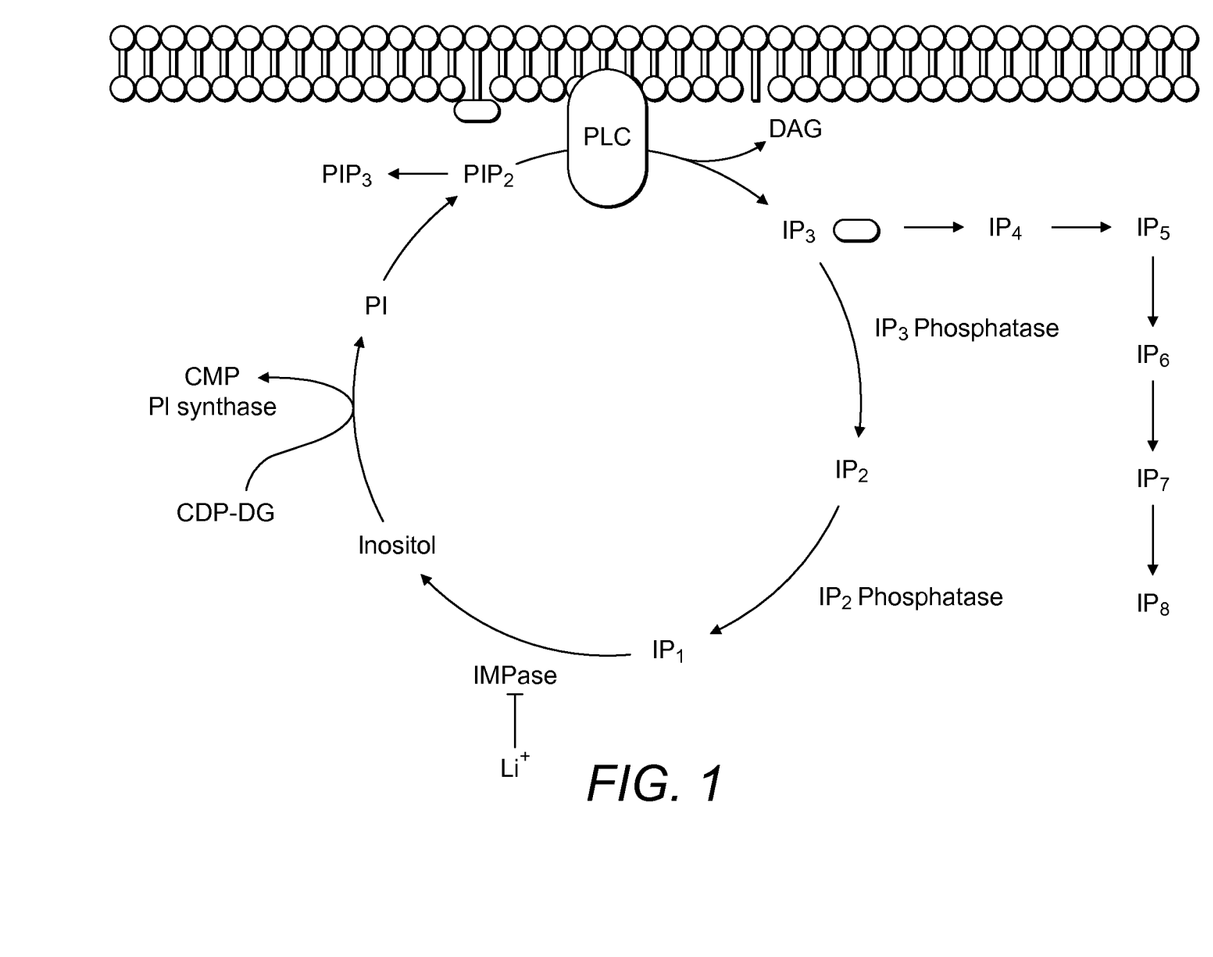
FIG. 1 is a simplified representation of the phosphoinositide (PI) pathway.

It is believed that the ability to inhibit the enzyme inositol monophosphatase (IMPase) is a key factor in the control of bipolar disorder. IMPase catalyses the hydrolysis of inositol monophosphate ($IP_1$) to inositol, and is required for regeneration of membrane phospholipids having an inositol head group. Hydrolysis of the head group of the phospholipid inositol 4,5-bisphosphate (PIP2) releases inositol 1,4,5-triphosphate (IP3) and diacyl glycerol (DAG). IP3 diffuses into the cytosol, and opens calcium channels to increase calcium. DAG stays in the membrane and activates protein kinase C. The enzyme phospholipase C (PLC) catalysis the hydrolysis of PIP2, and is under hormonal and neurotransmitter control. It is thought that inhibiting these signalling cascades in the phosphoinositide pathway (PI) is why lithium helps in bipolar disorder, by controlling certain populations of neurons which are overactive. This is illustrated in FIG. 1.

Berridge et al, in Cell, 59, 411-419, 1989, suggest that IMPase inhibition is the most plausible reason why lithium is successful in treating bipolar disorder. In WO 2009/138987, it was suggested that a dodecapeptide that had demonstrable IMPase inhibition activity could have potential utility in treating mood disorders. Additionally, WO96/37197 describes the use of tropolone derivatives as inhibitors of IMPase, and also their potential use in the treatment of mania and depression. Giocebbe et al in U.S. Pat. No. 4,981,980 further report that fermentation of a nutrient medium by a hypomycetes fungus of the genus Memnoniella or Stachybotrys yields a product, the major component of which can inhibit inositol monophosphatase, and is useful in the treatment of manic depression.

Atack et al, in Medicinal Research Reviews, 17(2), 1997, pp 215-224, proposed that the side-effects of lithium could be associated with its non-specificity to the IMPase enzyme, and attempted to develop new, specific inhibitors of IMPase based on analogues of the substrate, inositol. However, the compounds prepared either suffered from poor inhibition, or from poor bio-permeability.

Ebselen (2-phenyl-1,2-benzisoselenazol-3(2H)-one) is a known compound that has antioxidant activity (Muller et al; Biochemical Pharmacology, 33(20), 3235-3239, 1984), and has also been reported as being active in treating a number of therapeutic indications, for example as an antidepressant (Posser et al; European Journal of Pharmacology, 602, 85-91, 2009), for prevention and treatment of infectious diseases, for treatment of malignant tumours, for stimulating the immune system, for treating selenium deficiency diseases, for anti-arteriosclerotic and anti-inflammatory treatments (U.S. Pat. No. 5,021,242), in treating side-effects caused by medical use of cisplatin (WO92/02221), in treating noise-induced hearing loss (Lynch et al, Seminars in Hearing, 30(1), 47-55, 2009) and in treating mental illnesses that are treatable by promoting release of zinc from metallothionein, such as depression and schizophrenia (WO 99/49680). Its use in the treatment of cancer is also reported in US 2006/211745. It has been evaluated in phase III clinical trials for other disorders such as stroke and atherosclerosis, and is thus believed to be safe for use in humans.

None of these documents report the capability of ebselen, or analogues thereof, to act as an inhibitor of IMPase, and hence do not teach or disclose the use of ebselen or analogues thereof in treating conditions that are treatable through inhibition of the IMPase enzyme, such as bipolar disorder.

BRIEF SUMMARY OF THE INVENTION

According to the present invention, there is provided a compound of Formula I, or a pharmaceutically acceptable salt thereof, for use in the treatment of conditions that are treatable by inhibition of the enzyme inositol monophosphatase (IMPase), such as bipolar disorder, in which Formula I is:

Formula I in which:

E is S or Se and each of phenyl rings A and B is optionally substituted with one or more substituents, in which each substituent is selected independently from:

(1) a halogen, which is preferably selected from F, Cl and Br;

(2) $C_1$-$C_4$ alkyl, such as $C_1$-$C_2$ alkyl or $C_1$ alkyl, optionally substituted with one or more halogen atoms, each of which is preferably selected from F, Cl and Br; and (3) $C_1$-$C_4$ alkoxy, such as $C_1$-$C_2$ alkoxy or $C_1$ alkoxy; optionally substituted with one or more halogen atoms, each of which is preferably selected from F, Cl and Br.

Also provided is the use of a compound of Formula I, or a pharmaceutically acceptable salt thereof, in the treatment of conditions that are treatable through inhibition of the enzyme inositol monophosphatase, such as bipolar disorder.

There is additionally provided the use of a compound of Formula I, or pharmaceutically acceptable salt thereof, in the manufacture of a medicament for the treatment of conditions treatable by inhibition of the enzyme inositol monophosphatase (IMPase), such as bipolar disorder.

There is further provided a method for treating conditions treatable by inhibition of the enzyme inositol monophosphatase (IMPase), such as bipolar disorder, comprising administering to a patient in need thereof a therapeutically effective amount of a compound of Formula I, or pharmaceutically acceptable salt thereof.

One example of a compound of Formula I is 2-phenyl-1,2-benzisoselenazol-3(2H)-one, otherwise known as ebselen. Its structure is shown in Formula II.

Formula II

Another example of a compound of Formula I is 2-phenyl-1,2-benzisothiazol-3(2H)-one. Its structure is shown in Formula III below:

Formula III

Desirable features of the compounds described herein are the ability to inhibit IMPase, and hence they can be used to treat conditions that can be treated by inhibition of IMPase. Bipolar disorder is one such condition. The compounds described herein are bio-available and capable of transferring across the blood/brain barrier. Additionally, in contrast to lithium, they are considered to be less toxic than lithium, and more specific to inhibition of IMPase. Ebselen, for example, has already been through pre-clinical trials for other indications.

The hydrogen atoms of either one or both the phenyl rings A and B in the compound of Formula I can optionally be substituted with one or more substituents. Each substituent is independently selected from:

(1) a halogen, which is preferably selected from F, Cl and Br, more preferably from F and Cl;

(2) $C_1$-$C_4$ alkyl, such as $C_1$-$C_2$ alkyl or $C_1$ alkyl, optionally substituted with one or more halogen atoms, each of which is preferably selected from F, Cl and Br, more preferably from F and Cl; and (3) $C_1$-$C_4$ alkoxy, such as $C_1$-$C_2$ alkoxy or $C_1$ alkoxy; optionally substituted with one or more halogen atoms, each of which is preferably selected from F, Cl and Br, more preferably from F and Cl.

Each of phenyl rings A and B preferably comprises no more than 2 substituents, more preferably no more than 1 substituent. Even more preferably, only one of the phenyl rings A and B is substituted, and with no more than one substituent. Most preferably, both phenyl rings A and B are unsubstituted.

The compound has the structure of Formula I, or is a pharmaceutically acceptable salt thereof. In a preferred embodiment, the compound is not a salt.

The compounds of Formula I described herein, or pharmaceutically acceptable salts thereof, can be delivered to a patient by intradermal, intramuscular, intraperitoneal, intravenous, subcutaneous, intranasal, or oral routes, for example. They can be administered by any convenient means, for example by infusion or bolus injection, by absorption through epithelial or mucotaneous linings (e.g. oral mucosa, rectal and intestinal mucosa). Administration can be systemic or local.

The compounds of Formula I described herein, or pharmaceutically acceptable salts, thereof, can be formulated as a medicament, which preferably takes the form of therapeutically effective individual doses of the compound of Formula I or salt thereof, adjusted to the form of administration.

For oral administration, the medicament can be formulated into solid or liquid preparations, such as pills, tablets, troches, capsules, powder, granules, syrups, solutions, suspensions or emulsions.

Solid medicaments can comprise one or more of the following in addition to the desired quantity of the compound of Formula I or salt thereof: a pharmaceutically active carrier, including conventional ingredients such as lactose, sucrose and cornstarch; binders such as acacia, cornstarch or gelatine; disintegrating agents, such as potato starch or alginic acid; and lubricants such as stearic acid or magnesium stearate. Optionally, the medicament can be a sustained release formulation, in which the ebselen is incorporated in a matrix of an acrylic polymer or chitin, for example.

Examples of liquid medicaments for oral administration include aqueous solutions such as syrups, flavoured syrups, aqueous or oil suspensions, optionally flavoured emulsions with edible oils, and elixirs. Suspensions can include dispersing or suspending agents such as synthetic and natural gums, for example tragacanth, acacia, alginate, dextran, sodium carboxymethylcellulose, methylcellulose, polyvinylpyrrolidione and gelatin.

For parenterally-administered medicaments, the compound of Formula I or salt thereof is typically formulated with a suitable liquid injection vehicle, which include for example water, saline, dextrose, water-miscible solvents such as ethanol, polyethylene glycol and propylene glycol, and non-aqueous vehicles such as plant or animal oils. Optionally, the medicament can be an emulsion. Optionally, the pH is typically in the range of from 6 to 8, preferably 6.5 to 7.5. Optionally, buffers such as citrates, acetates or phosphates, can be present. Optionally, antioxidants such as ascorbic acid or sodium bisulphite can be present. Optionally, solubilising agents and stabilisers such as cyclodextrin, lysolecithin, oleic acid, stearic acid, and dextrin can be present. Optionally, local anaesthetics such as lignocaine and procaine hydrochloride-can be present. Formulations such as those described in US 2004/0029934, comprising phosphatidylcholine and phosphatidylethanolamine, and those described in US 2004/0053888 comprising cyclodextrin, can be used.

Suitable doses of the compound of Formula I or salt thereof are in the range of from 5 to 5000 mg for a human patient per day, for example from 50 to 2000 mg per day or 500 to 1000 mg per day.

The compound of Formula I or salt thereof can be provided in one dose, or more than one dose, typically in the range of from two to eight doses per day, for example from two to four or from two to three doses per day. In one embodiment, the compound of Formula I or salt thereof can be administered in the form of an orally administered solution or suspension in water. An example of a dosage regime would be the administration of a solution or suspension comprising 100 mg of the compound of Formula I or salt thereof in water 3 times per day, or 150 mg in water twice daily. In another embodiment, capsules, pills or tablets comprising the compound of Formula I or salt thereof for oral administration can be provided, for example the administration of 1, 2, 4 or 8 capsules, pills or tablets each comprising 200 mg of the compound of Formula I or salt thereof per day. The compounds or salts described herein can be administered in combination with one or more further compounds that are effective for use in treating bipolar disorder, for example one or more of valproic acid, lamotrigine, carbamazapine, another compound of Formula I described herein, pharmaceutically acceptable salts of any one or more thereof, and pharmaceutically acceptable salts of lithium. Administration can be simultaneous, sequential or separate, and can be provided in the form of a kit comprising the two or more active ingredients, either combined together in a single medicament, or separately in the form of separate medicaments.

Ebselen and 2-phenyl-1,2-benzisothiazol-3(2H)-one are particularly preferred compounds.

The bio-permable properties of ebselen, enabling it to transfer across the blood/brain barrier, are demonstrated by the examples below. Ebselen is also known to be sufficiently non-toxic in humans at pharmaceutically effective dosages, and hence is a strong candidate for future clinical trials in the treatment of disorders that are treatable by IMPase inhibition, bipolar disorder being an example. The $LD_{50}$ concentration of ebselen is greater than 1000 mg/kg in rats. Its relatively low toxicity compared to lithium is thought to be due to its greater specificity towards IMPase inhibition. Ebselen has an $IC_{50}$ (the concentration at which 50% inhibition is achieved) for IMPase of about 2 μM. The corresponding value for 2-phenyl-1,2-benzisothiazol-3(2H)-one is 35 μM.

Ebselen and 2-phenyl-1,2-benzisothiazol-3(2H)-one can be provided in the form of a pharmaceutically acceptable salt. They can each be formulated as outlined above, and in the dosages as described above.

BRIEF DESCRPTION OF THE DRAWINGS

The invention will now be illustrated by the following non-limiting examples, and with reference to the Figures in which.

In the bar charts of FIGS. 6, 8 and 10, the "*", "**" and "ns" signify the statistical t-test of the means, where "*" denotes $p<0.05$, "**" denotes $p<0.001$, and "ns" denotes "not significant".

DETAILED DESCRPTION OF THE INVENTION

Human inositol monophosphatase cDNA was ordered from Geneservice, Source Bioscience, Cambridge, UK. The cDNA was inserted into plasmid pRSET5a, which was then transformed into JM109 competent cells. These cells were allowed to multiply and the plasmid was then extracted from the cells. The plasmid was then transformed into expression bacteria, *E.coli* strain BL21 (DE3) pLysS. Protein expression was optimized and the best yield of inositol monophosphatase was found to be under the following conditions: expression bacteria grown in lactose broth containing 2.5 mM betaine and 660 mM sorbital to an OD of 0.9, followed by induction with 0.4 mM Isopropyl alpha-D-1-thiogalactopyranoside (IPTG), which was then left overnight at 30° C. in an incubator. The next day the cells were lysed and the soluble fraction, which contained the enzyme, was collected. Purification was carried out in 3 stages. The soluble fraction was heated at 68° C. for 1 hour and then centrifuged. The supernatant was taken and run through a Q-sepharose column (Pharmacia). Different fractions were collected and assessed for activity. The active fractions were then passed through a Tricorn MonoQ 5/50 GL column (GE Healthcare, UK) for further purification.

Each enzymatic reaction using human inositol monophosphatase contained 0.00013 mg of enzyme (0.0673 mg/mL). The substrate inositol monophosphate (Alexis Chemicals) was diluted with the appropriate buffer to make up a concentration of 50 mM stock. The stock was then diluted with buffer to yield the following concentrations of substrate: 0 mM, 0.1 mM, 0.5 mM, 1.0 mM, 1.5 mM, 2.5 mM, 5 mM, 10 mM, 20 mM, 25 mM and 30 mM. From this 2 μL of substrate was added to each reaction well giving a tenfold dilution of substrate to 0 mM, 0.01 mM, 0.05 mM, 0.1 mM, 0.15 mM, 0.25 mM, 0.5 mM, 1 mM, 2 mM, 2.5 mM and 3 mM. The reaction buffer contained 1 mM EGTA, 150 mM KCl, 3 mM $MgCl_2$, 0.5 ng/mL BSA, 50 mM Tri, HCl, pH 7.4 and 0.01% Triton X100.

A malachite green assay was used for the quantitative determination of free inorganic phosphate present at the end of the IMPase reaction. This involved dissolving 4.2% w/v ammonium molybdate in 4M hydrochloric acid. The Malachite Green itself was made up to 0.045% w/v concentration. From these stocks, a 3:1 malachite green:ammonium molybdate mixture was prepared and vortexed for thirty minutes. The malachite green forms a complex of ammonium molybdate:malachite green:inorganic phosphate in the presence of free inorganic phosphate. To each reaction plate, duplicate wells of a range of known phosphate concentrations were prepared within the concentration range of 0-300 μM with each well containing 20 μL of solution. The phosphate standards were made from serial dilutions of 1M potassium dihydrogen phosphate using double distilled $H_2O$. To each well was added 180 μL of malachite green:ammonium molybdate mix. The colour produced by the reaction between the inorganic phosphate and malachite green:ammonium molybdate was proportional to the amount of phosphate present. The colour was allowed to develop for 15 min and then the plate was read on a TECAN Sunrise microplate reader at 595 nm wavelength.

Figure 2:
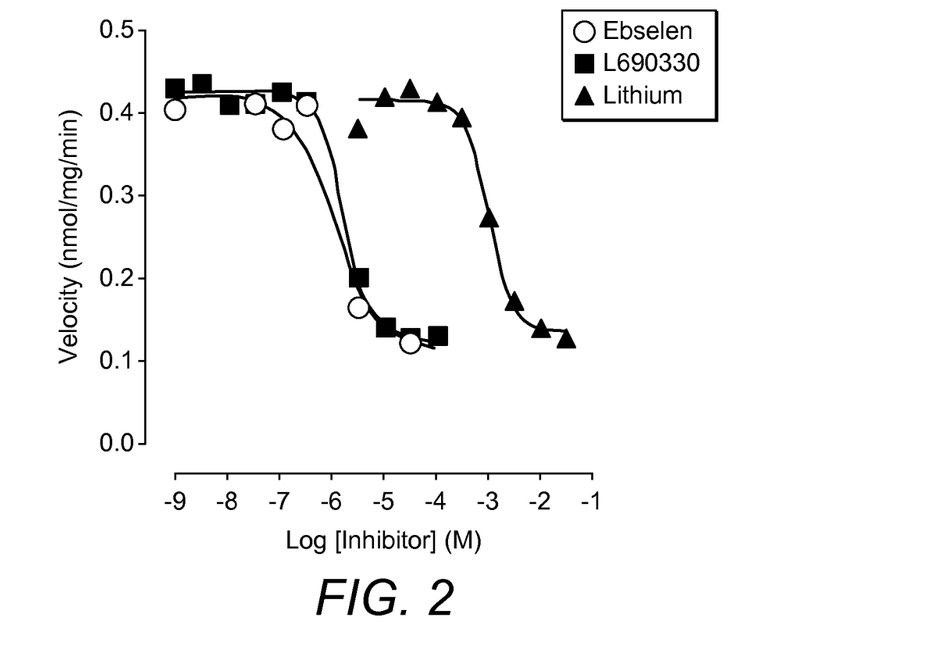
FIG. 2 is a graph showing the in vitro IMPase inhibition effects of ebselen (unfilled circles), lithium (filled triangles) and compound L690330 (filled squares) as described by Atack et al in Medicinal Research Reviews, 17(2), 1997, 215-224).

For the reactions whose results are shown in FIG. 2, lithium (Sigma) was dissolved in double-distilled $H_2O$ and diluted appropriately to the concentration of 10 mM with 2 μL of lithium being added per well to yield a final well concentration of 1 mM. Stock concentrations of lithium were also made from this. L690330 was purchased from Sigma Chemicals, and was made up to a 1 mM stock concentration using $H_2O$.

From this stock the following concentrations were prepared using serial dilutions with water: 300 μM to 30 nM. These concentrations were used to produce a concentration-inhibition curve for the enzyme. Ebselen was purchased from from BioFocus as a 10 mM stock in DMSO.

The experiments used to obtain the data for FIG. 2 were all carried out in the presence of a constant amount of inositol monophosphate. Data for ebselen are represented by circles, L690330 by squares, and lithium by triangles.

The ebselen had an $IC_{50}$ of about 2 μM. L690330, which is reported to have an $IC_{50}$ of about 300 nM for bovine IMPase, was shown in the present study to have a higher $IC_{50}$ value (1.5 μM) for human IMPase.

Figure 3:
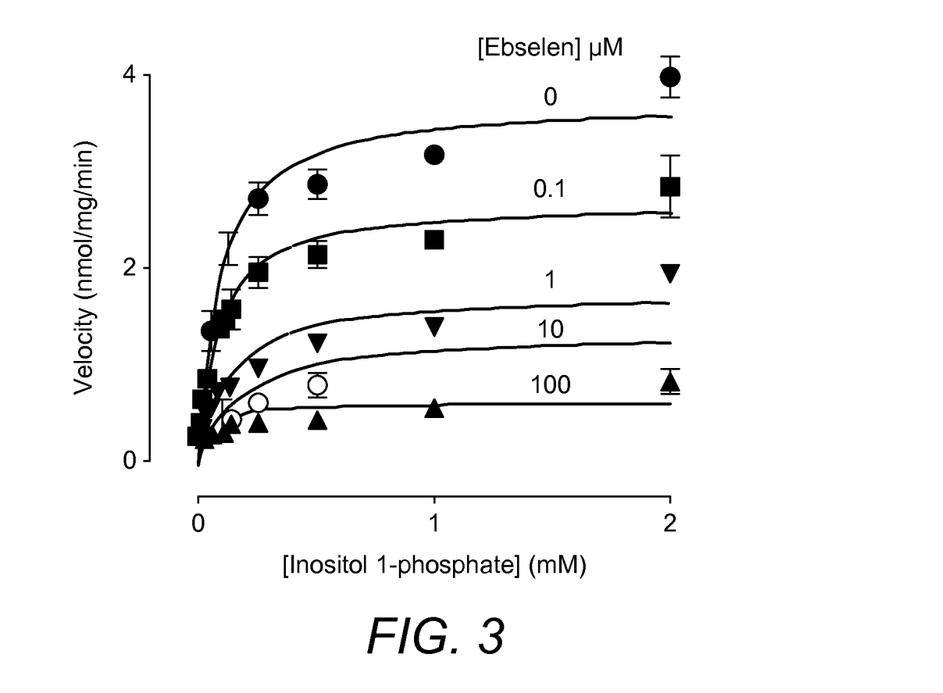
FIG. 3 is a graph showing the effects of different ebselen concentrations on IMPase inhibition in vitro.

FIG. 3 shows the effect of increased concentrations of ebselen on IMPase inhibition, the rate of the IMPase-catalysed reaction decreasing with increased ebselen concentrations. The experiment was based on measuring the extent of enzymatic cleavage of inositol monophosphate by the purified human IMPase enzyme in the presence of various concentrations of ebselen. The results demonstrate that increasing the concentration of the inositol monophosphate substrate does not overcome ebselen-mediated inhibition, indicating a non-competitive mode of inhibition.

Figure 4:
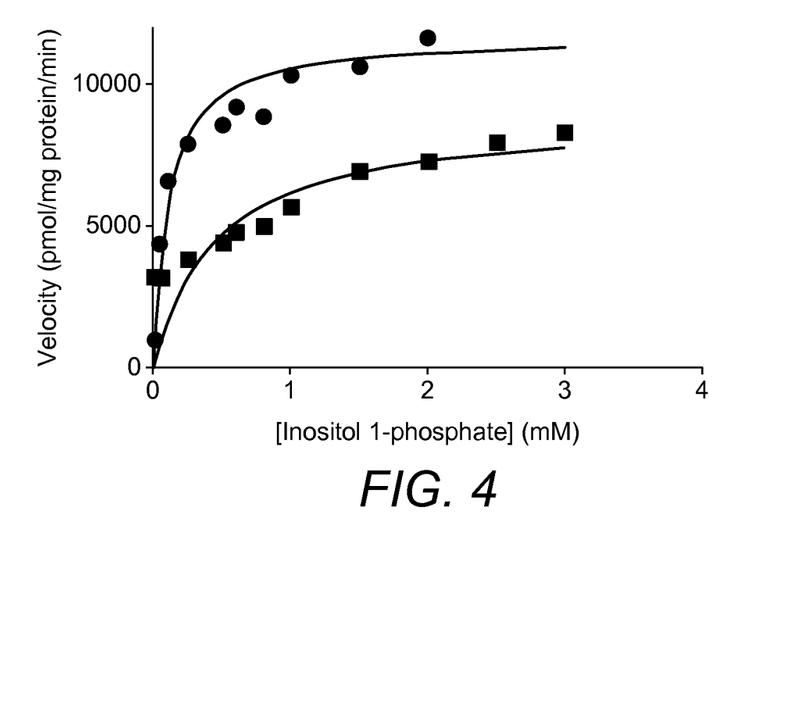
FIG. 4 is a graph showing the effects of 2-phenyl-1,2-benzisothiazol-3(2H)-one on IMPase inhibition in vitro.

FIG. 4 shows that in vitro inhibition of IMPase is also achieved using 2-phenyl-1,2-benzisothiazol-3(2H)-one. These experiments were carried out in an analogous way to the experiments for ebselen above, except that the concentration of the 2-phenyl-1,2-benzisothiazol-3(2H)-one used was 30 μM.

L690330 is reported by Atack et at as not being bio-available. To determine the bio-availability of ebselen, a mouse ex vivo assay was used. In this assay mice were given an intraperitoneal (i.p.) injection of 5 mg/kg ebselen solublized in betacyclodextrin, according to the following procedure. A stock solution of 0.5 M ebselen in DMSO and a stock of 40% 2-Hydroxy propyl-beta-cyclodextrin (HPBCD) were made. A 3.5 mM solution of ebselen (from 0.5 M stock) was made into 40% HPBCD and finally, to obtain the concentration of 350 μM ebselen, a 1 in 10 dilution was carried out. A control solution was made containing the same dilution of DMSO and HPBCD. The volume of drug/vehicle injected i.p. into the mouse was 1 ml (for the animals dosed with ebselen this is approximately 5 mg/kg assuming each mouse weighs about 20 g). CD1 male mice, weighing approximately 20 g were used. The animals were dosed for one hour with either drug or vehicle before being killed by cervical dislocation. The brains were quickly dissected out and frozen in liquid nitrogen. At a later time, the brains were thawed and then homogenized in 500 μL of intracellular buffer containing 0.25 M sucrose, 20 mM triethylamine, 20 μg/ml of soybean trypsin inhibitor, and protease inhibitor tablets.

The protein concentration of each brain homogenate was determined and a stock of 2.5 mg of protein was made from the homogenate and stored. For the inositol monophosphatase activity assay, 10 μL of this brain homogenate was taken in eppendorfs and incubated with 2 μL of varying concentrations of inositol monophosphate. The volume was made up to 50 μL with Tris buffer to give a final protein concentration of 0.5 mg. The eppendorf was placed in a water bath at 37° C. for 1 hour with shaking at 20-min intervals. After 1 h, an equal volume of ice cold methanol was added in order to precipitate out the proteins and the eppendorfs were centrifuged. 20 μL of the supernatant was placed in a 96-well plate and 180 μL of a 3:1 mixture of 0.045% malachite green: 4.2% ammonium molybdate in 4 M HCl was added. The intensity of the green color formed was measured at 595 nm.

Figure 5:
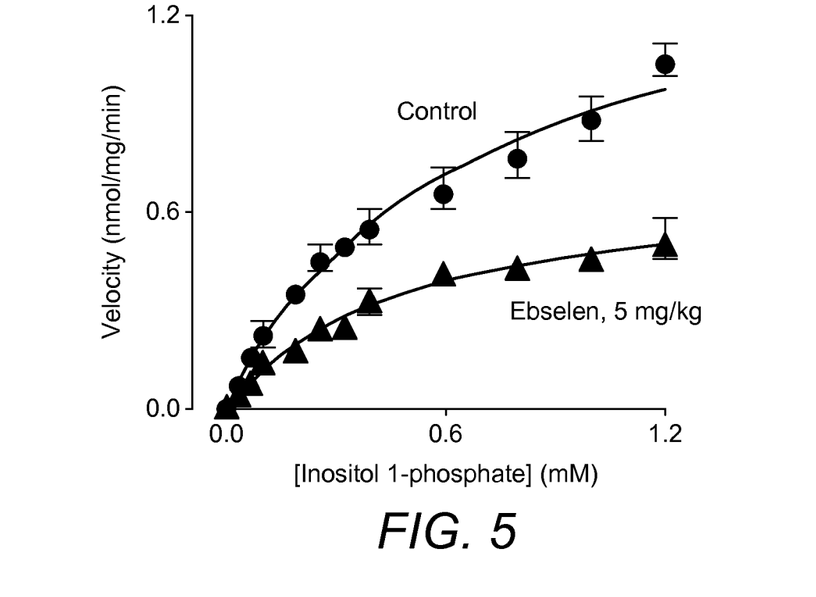
FIG. 5 is a graph of ex vivo results showing reduced IMPase activity in homogenised mouse brains after the mice were injected with 5 mg/kg of either ebselen or a control.

The amount of phosphate detected was found to be significantly lower for the ebselen-injected mice compared to the control as shown in FIG. 5 (ebselen, lower line, triangles; control, upper line, circles). This suggests that the drug treated mice, had lower inositol monophosphatase activity than the control mice. The data also demonstrate that ebselen is bio-available, being blood/brain barrier permeable, and active in the intact animal and inhibits endogenous IMPase.

Figure 6:
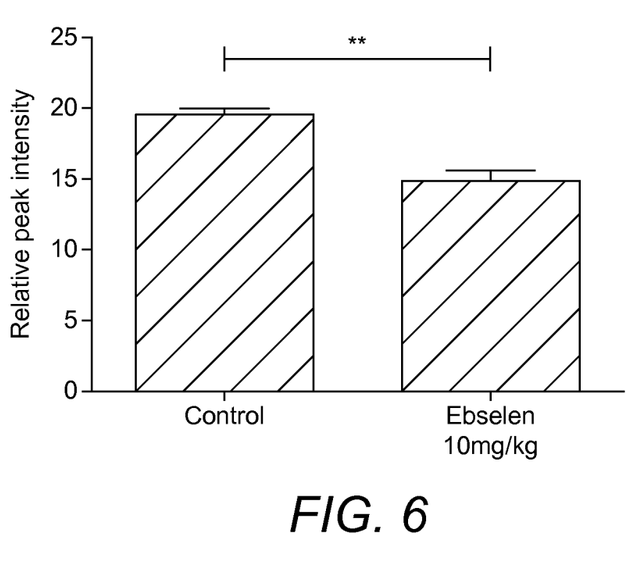
FIG. 6 is a bar chart showing ex vivo measurements of inositol levels in mice brains 1 hour after intraperitoneal injection of either ebselen or control.

Similar conclusions can be reached from the results shown in FIG. 6, in which inositol levels in mice brains were measured ex vivo using $^1$H NMR spectroscopy. The results were obtained from brains removed from mice 1 hour after intraperitoneal injection either with ebselen or with a control. Inositol levels in the brain were significantly lower in the ebselen-treated mice (p<0.001), suggesting increased IMPase inhibition.

Activity and monitoring evaluation of mice was also studied. Mice were given an i.p. injection with saline (control) or ebselen (1, 5 or 10 mg/kg) and placed in a 35×35 cm perspex arena where their location was recorded by the Ethovision videotracking system (Noldus, Wageningen, The Netherlands). After 60 minutes, the mice were injected with d-amphetamine (4 mg/kg) or control. The Ethovision system follows the centre of the body of the mouse and records its position according to the location of this point. Data analysis was performed by Ethovision software, and distances moved within each 5 minute interval were calculated and plotted. The total distance moved was computed for the time frame from 60 to 120 minutes following the beginning of data acquisition. Amphetamine-induced hyperactivity is used as an animal model of mania, and is sensitive to mood-stabilising drugs such as lithium.

Figure 7:
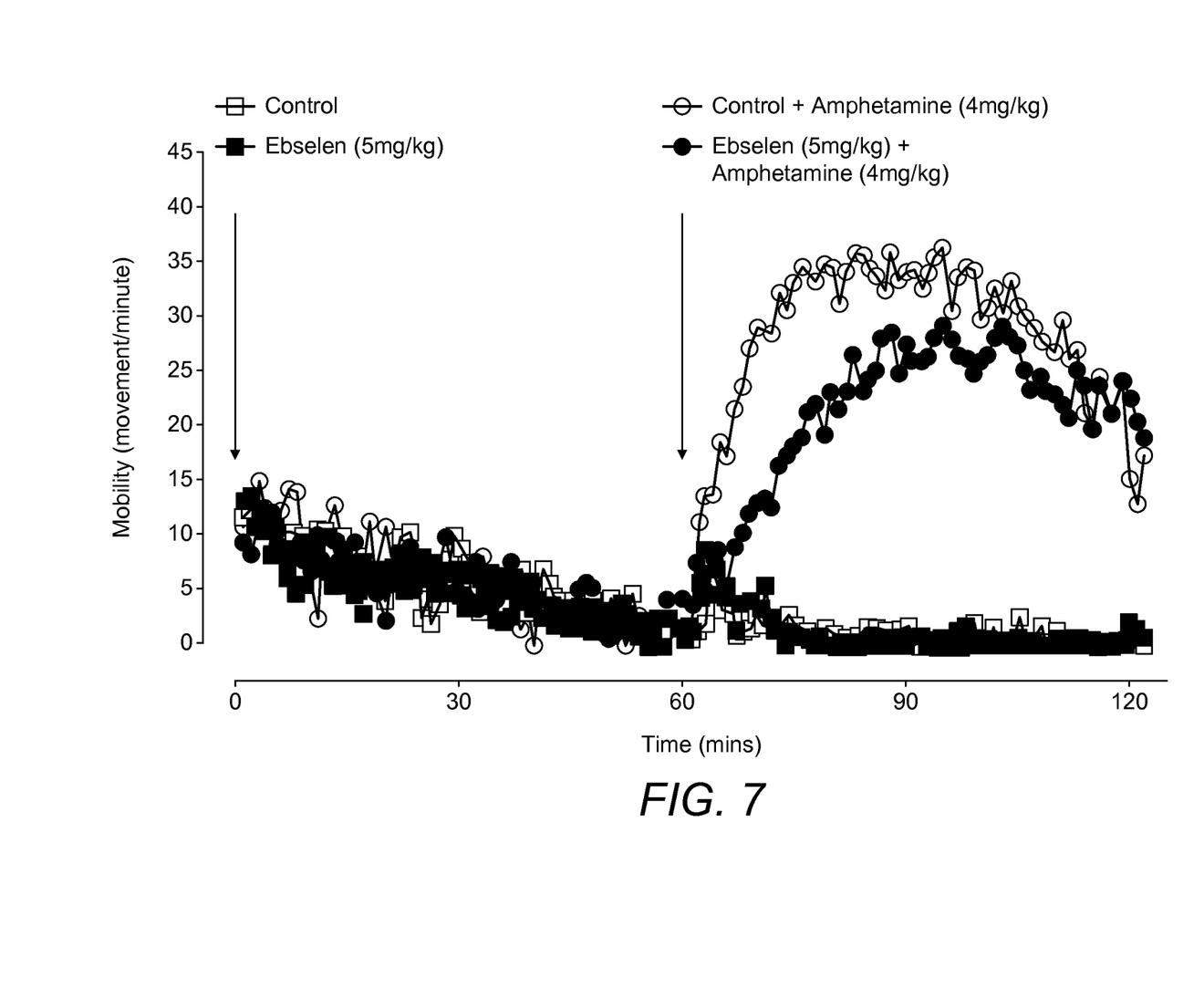
FIG. 7 is a graph of mobility versus time of mice after administration of amphetamine and/or ebselen.
Figure 8:
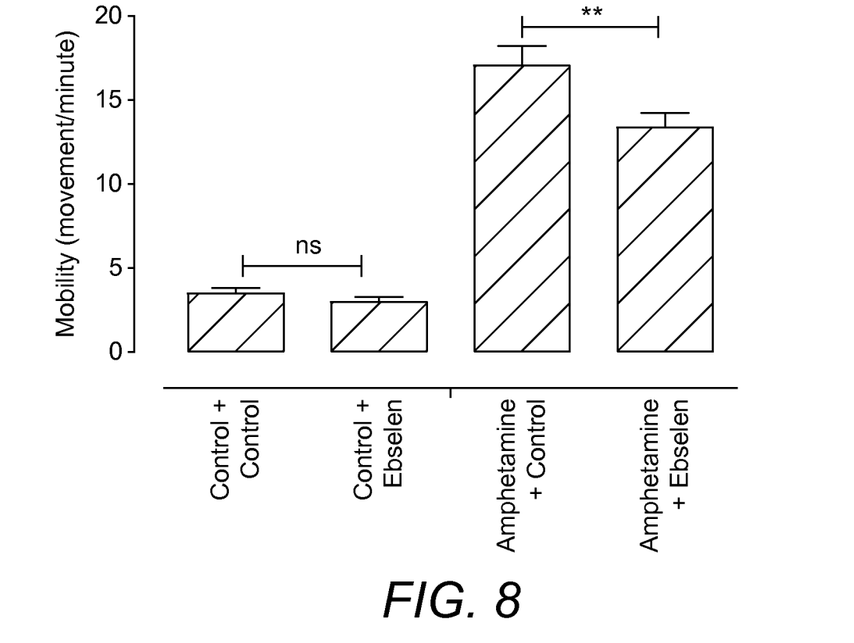
FIG. 8 is a bar chart showing average activity of ebselen or control-treated mice after administration of either d-amphetamine or control.

FIG. 7 shows activity patterns before and after injection of either the amphetamine or the control for ebselen- and control-treated mice. FIG. 8 shows the average movement observed in the period 60 to 120 minutes, i.e. the period after injection of the d-amphetamine or control. These Figures demonstrate that the ebselen-treated mice have a reduced level of amphetamine-induced hyperactivity (p<0.001).

Rearing experiments were also carried out as follows. Mice were allowed to move freely within a caged equipped with infrared beam lines placed at two heights.

Figure 9:
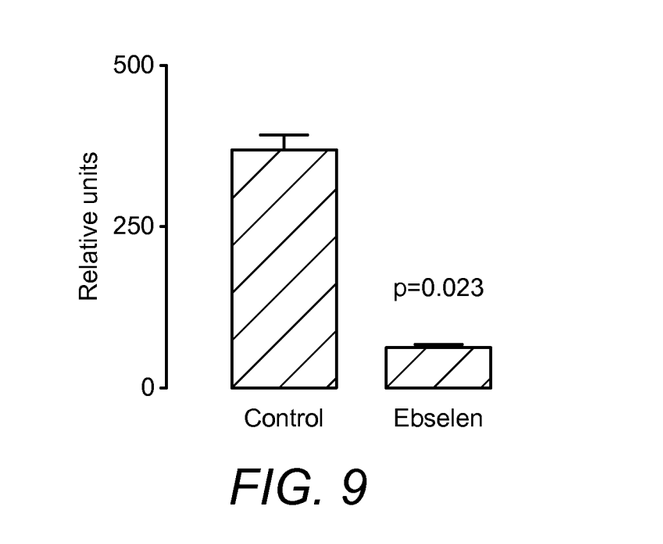
FIG. 9 is a bar chart highlighting the inhibitory effects of ebselen on rearing behaviour in mice.

Mice could only break the upper beams by rearing. The data in FIG. 9 show the number of beam breaks during the open-field test were significantly reduced in the ebselen-treated mice (p=0.023).

If ebselen is mimicking the action of lithium, it would be expected to have lithium-like effects on rodent behaviour. Ebselen induced a decrease in rearing (FIG. 9) and a decrease in amphetamine-induced hyperlocomotion (FIGS. 7 and 8). Both rearing and amphetamine-induced hyperlocomotion are behavioural tests that are more selective to lithium than other antidepressants and diagnostic for lithium-like activity. Therefore, ebselen not only inhibits the enzyme IMPase in vitro and ex vivo but also mimics the effect of lithium in whole mouse behaviour. Combined, these results are consistent with the action of lithium being through IMPase, and that ebselen is an effective lithium mimetic.

Figure 10:
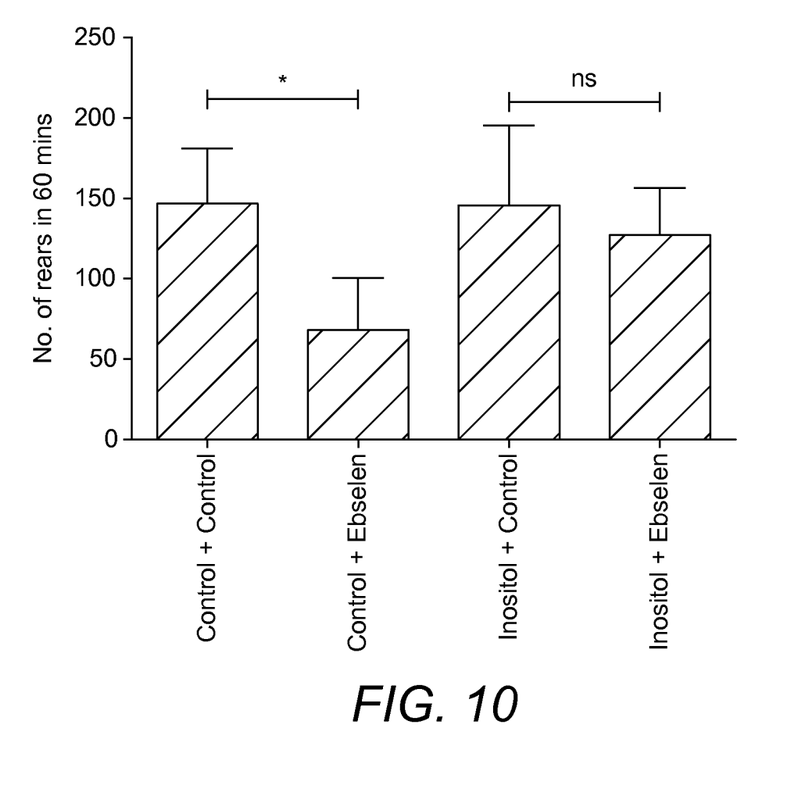
FIG. 10 is a bar chart showing the changes in rearing behaviour of ebselen- and control-treated mice after injection of inositol.

This is confirmed by the results shown in FIG. 10. In these rearing experiments, mice were given an intraperitoneal injection of control or ebselen (5 mg/kg), and after 60 minutes were given an intracerebroventricular injection of control or 5.5 μmol inositol. The effects of ebselen on suppressing rearing behaviour were significantly reduced, consistent with ebselen acting as an inhibitor of IMPase.

Based on the low p-values associated with the results in FIGS. 6, 8, 9 and 10, there is a very low probability that the observed differences occurred purely by chance.

Ebselen and 2-phenyl-1,2-benzisothiazol-3(2H)-one have been identified as small-molecule inhibitors of IMPase using in vitro screen against expressed human IMPase. In addition, ebselen has been demonstrated to be bio-available in an ex vivo assay using the brains of mice injected with ebselen.

Given that ebselen is a known compound that has been proved safe in man in clinical studies of stroke (Ogawa et al; Cerebrovasc. Dis., 9 112-118, 1999; Saito et al; Neurosurgery, 42, 269-277; Yamaguchi et al, Stroke, 29, 12-17, 1998), atherosclerosis (Clinical Trials.gov Identifier NCT00762671), pancreatitis (Lu et al, J. Organ Dysfunction, 4, 43-50, 2008) and the prevention of hearing loss (Lynch et al, Seminars in Hearing, 30(1), 47-55, 2009), ebselen should be able to enter clinical trails for bipolar disorder.

What is claimed is:

1. A method of treating bipolar disorder, wherein said method comprises administering to a patient in need thereof a therapeutically effective amount of a compound of Formula I, or a pharmaceutically acceptable salt thereof, wherein Formula I is:

Formula I in which:

E is S or Se and each of phenyl rings A and B is optionally substituted with one or more substituents, in which each substituent is selected independently from:
(1) a halogen;
(2) $C_1$-$C_4$ alkyl, optionally substituted with one or more halogen atoms; and
(3) $C_1$-$C_4$ alkoxy, optionally substituted with one or more halogen atoms.

2. The method of claim 1, wherein the amount of the compound of Formula I or pharmaceutically acceptable salt thereof administered to the patient is in the range of from 10 to 2000 mg per day.

3. The method of claim 2, in which the compound of Formula I, or pharmaceutically acceptable salt thereof, is provided in one or more than one dose per day.

4. The method according to claim 1, wherein the compound of Formula I, or pharmaceutically acceptable salt thereof, is administered in combination with one or more further compounds that are effective for treating bipolar disorder.

5. The method according to claim 4, wherein said one or more further compounds are selected from the group consisting of valproic acid, lamotrigine, carbamazapine, pharmaceutically acceptable salts of one or more thereof, pharmaceutically acceptable salts of lithium, and combinations thereof.

6. The method according to claim 4, wherein the compound of Formula I and said one or more further compounds are administered simultaneously, sequentially or separately.

7. The method as claimed in claim 1, wherein said compound is selected from the group consisting of (2-phenyl-1,2-benzisothiazol-3(2H)-one)

(2-phenyl-1,2-benzisoselenazol-3(2H)-one or ebselen)

8. The method as claimed in claim 7, wherein said compound is ebselen.

9. The method according to claim 1, wherein said halogen in (1) is selected from the group consisting of F, Cl and Br.

10. The method according to claim 1, wherein said $C_1$-$C_4$ alkyl is $C_1$-$C_2$ alkyl or $C_1$ alkyl.

11. The method according to claim , wherein said $C_1$-$C_4$ alkoxy is $C_1$-$C_2$ alkoxy or $C_1$ alkoxy.

12. The method according to claim 1, wherein said one or more halogen atoms in (2) or (3) is selected from the group consisting of F, Cl, and Br.

13. The method according to claim 2, wherein said amount of the compound of Formula I or pharmaceutically acceptable salt thereof is in the range of from 10 to 300 mg per day.

14. The method according to claim 3, wherein said compound of Formula I or pharmaceutically acceptable salt thereof is provided in two or three doses per day.

* * * * *